(12) United States Patent
Wennogle et al.

(10) Patent No.: US 11,440,911 B2
(45) Date of Patent: Sep. 13, 2022

(54) SALTS AND CRYSTALS

(71) Applicant: INTRA-CELLULAR THERAPIES, INC., New York, NY (US)

(72) Inventors: Lawrence P. Wennogle, Hillsborough, NJ (US); Peng Li, New Milford, NJ (US); Edwin Aret, Almere (NL)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 16/649,515

(22) PCT Filed: Sep. 26, 2018

(86) PCT No.: PCT/US2018/052922
§ 371 (c)(1),
(2) Date: Mar. 20, 2020

(87) PCT Pub. No.: WO2019/067591
PCT Pub. Date: Apr. 4, 2019

(65) Prior Publication Data
US 2020/0247805 A1    Aug. 6, 2020

Related U.S. Application Data

(60) Provisional application No. 62/563,341, filed on Sep. 26, 2017.

(51) Int. Cl.
*C07D 471/16* (2006.01)
(52) U.S. Cl.
CPC ........ *C07D 471/16* (2013.01); *C07B 2200/13* (2013.01)
(58) Field of Classification Search
CPC .......................... C07D 471/16; C07B 2200/13
See application file for complete search history.

(56) References Cited

U.S. PATENT DOCUMENTS

| | | | |
|---|---|---|---|
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,849,619 B2 | 2/2005 | Robichaud et al. |
| 7,071,186 B2 | 7/2006 | Robichaud et al. |
| 7,081,455 B2 | 7/2006 | Robichaud et al. |
| 7,183,282 B2 | 2/2007 | Robichaud et al. |
| RE39,679 E | 6/2007 | Robichaud et al. |
| 7,238,690 B2 | 7/2007 | Robichaud et al. |
| 7,462,641 B2 | 12/2008 | Igo et al. |
| 8,309,722 B2 | 11/2012 | Tomesch et al. |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,616,061 B2 | 4/2017 | Mates et al. |
| 9,708,322 B2 | 7/2017 | Peng et al. |
| 9,751,883 B2 | 9/2017 | Tomesch et al. |
| 9,956,227 B2 | 5/2018 | Vanover et al. |
| 10,077,267 B2 | 9/2018 | Mates et al. |
| 10,117,867 B2 | 11/2018 | Mates et al. |
| 10,322,134 B2 | 6/2019 | Vanover et al. |
| 10,702,522 B2 | 7/2020 | Mates et al. |
| 10,960,009 B2 | 3/2021 | Vanover et al. |
| 10,960,010 B2 | 3/2021 | Vanover et al. |
| 11,026,951 B2 | 6/2021 | Vanover et al. |
| 11,053,245 B2 | 7/2021 | Mates et al. |
| 11,124,514 B2 | 9/2021 | Mates et al. |
| 2010/0204470 A1* | 8/2010 | Wieser .................. C07C 209/68 544/138 |
| 2015/0072964 A1* | 3/2015 | Mates ....................... A61P 3/04 514/171 |
| 2015/0079172 A1 | 3/2015 | Mates et al. |
| 2015/0080404 A1 | 3/2015 | Mates et al. |
| 2018/0271862 A1 | 9/2018 | Li et al. |
| 2019/0112309 A1 | 4/2019 | Li et al. |
| 2019/0112310 A1 | 4/2019 | Li et al. |
| 2019/0211015 A1 | 7/2019 | Mittelman et al. |
| 2019/0231780 A1 | 8/2019 | Yao et al. |
| 2020/0102309 A1 | 4/2020 | Li et al. |
| 2020/0148683 A1 | 5/2020 | Peddy et al. |

FOREIGN PATENT DOCUMENTS

| WO | WO 2009/017836 A1 | 2/2009 |
| WO | WO 2009/145900 | * 12/2009 |
| WO | WO 2019/102240 A1 | 5/2019 |

OTHER PUBLICATIONS

Li et al. in Journal of Medicinal Chemistry 57, 2670-2682 (2014) (Year: 2014).*
Bastin et al. in Organic Process Research & Development 2000, 4, 427-435 (Year: 2000).*
Balbach, et al. "Pharmaceutical evaluation of early development candidates 'the 100 mg-approach'," International Journal of Pharmaceutics, vol. 275, pp. 1-12 (2004).
Bastin, "Salt Selection and Optimized Procedures for Pharmaceutical New Chemical Entities", Organic Process and Research Development, vol. 4, No. 5, pp. 427-435 (2000).
Byrn, "Pharmaceutical Solids: A Strategic Approach to Regulatory Considerations," vol. 12, No. 7, pp. 945-954 (1995).
Caira M.R., "Crystalline Polymorphism of Organic Compounds," Design of Organic Solids, Topics in Current Chemistry, 198:163-208 (1998).

(Continued)

*Primary Examiner* — Jared Barsky
(74) *Attorney, Agent, or Firm* — Hoxie & Associates LLC

(57) ABSTRACT

The disclosure provides new, stable, pharmaceutically acceptable hydrochloride salt forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one, together with methods of making and using them, and pharmaceutical compositions comprising them.

5 Claims, 4 Drawing Sheets

(56) References Cited

OTHER PUBLICATIONS

Davis, et al. "ITI-007 demonstrates brain occupancy at serotonin 5-HT2A and dopamine D2 receptors and serotonin transporters using positron emission tomography in healthy volunteers," Psychopharmacology, Published Online Apr. 7, 2015, 10 pages.

Davis, et al., "ITI-007 in the treatment of schizophrenia: from novel pharmacology to clinical outcomes," Expert Review of Neurotherapeutics, vol. 16, No. 6, pp. 601-614 (2016).

Gadade, et al., "Pharmaceutical Cocrystals: Regulatory and Strategic Aspects, Design and Development," Adv Pharm Bull, vol. 6, No. 4, pp. 479-494, (2016).

Grant, "Polymorphism in Pharmaceutical Solids", Chapter 1, pp. 1-10 (1999).

Guillory, "Polymorphism in Pharmaceutical Solids", Chapter 5, pp. 183-226 (1999).

Haynes, "Occurrence of Pharmaceutically Acceptable Anions and Cations in the Cambridge Database," Journal of Pharmaceutical Sciences, vol. 94, No. 10, pp. 2111-2120 (2005).

International Search Report for International Application No. PCT/US2018/052922, dated Nov. 26, 2018, 3 pages.

Jain, et al., "Polymorphism in Pharmacy", Indian Drugs, vol. 23, No. 6, pp. 315-316 (1986).

Lee, et al., "Novel, Highly Potent, Selective 5-HT2A/D2 Receptor Antagonists as Potential Atypical Antipsychotics," Bioorg. Med. Chem. Lett., vol. 13, p. 767-770, (2003).

Li, et al., "Discovery of a Tetracyclic Quinoxaline Derivative as a Potent and Orally Active Multifunctional Drug Candidate for the Treatment of Neuropsychiatric and Neurological Disorders," vol. 57, pp. 2670-2682 (2014).

Li, et al., "Dopamine Targeting Drugs for the Treatment of Schizophrenia: Past, Present and Future," Current Topics in Medicinal Chemistry, vol. 16, pp. 3385-3403 (2016).

Marek, et al., "Synergistic Action of 5-HT2A Antagonists and Selective Serotonin Reuptake Inhibitors in Neuropsychiatric Disorders," Neuropsychopharmacology, vol. 28, pp. 402-412 (2003).

Nagai, et al., "Synthesis of 2, 3, 4, 4a, 5, 9b-hexahydro-1H-pyrido [4,3-b] indole derivatives and their central nervous system activities." Journal of Medicinal Chemistry, vol. 22, No. 6, pp. 677-683, (1979).

Newman, et al., "Solid-State Analysis of the Active Pharmaceutical Ingredient in Drug Products," Drug Discovery Today, vol. 8, No. 9, pp. 898-903 (2003).

Savjani et al., "Drug Solubility: Importance and Enhancement Techniques," International Scholarly Research Network Pharmaceutics (2012), vol. 2012, pp. 1-10.

Singhal, et al., "Drug polymorphism and dosage form design: a practical perspective", Advanced Drug Delivery Reviews, vol. 56, pp. 335-347 (2004).

Snyder, et al., "Functional Profile of a Novel Modulator of Serotonin, Dopamine, and Glutamate Neurotransmission," Psychopharmacology, vol. 232, pp. 605-621 (2015).

Vippagunta, et al., "Crystalline Solids," Advanced Drug Delivery Reviews, vol. 48, 24 pages, (2001).

\* cited by examiner

SALTS AND CRYSTALS

CROSS-REFERENCE TO RELATED APPLICATIONS

This application is a U.S. National Stage application under 35 U.S.C. § 371 of International Application No. PCT/US2018/052922, filed on Sep. 26, 2018, which claims priority to and the benefit of U.S. Provisional Application No. 62/563,341, filed on Sep. 26, 2017, the contents of which are hereby incorporated by reference in its entirety.

FIELD

This disclosure relates to certain novel salts and crystal forms of a substituted heterocycle fused gamma-carboline, the manufacture thereof, pharmaceutical compositions thereof, and use thereof, e.g., in the treatment of diseases or abnormal conditions involving or mediated by the 5-$HT_{2A}$ receptor, serotonin transporter (SERT), and/or dopamine $D_1/D_2$ receptor signaling pathways.

BACKGROUND 1-(4-fluoro-phenyl)-4-(((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, and also known as Lumateperone or as ITI-007), has the following structure:

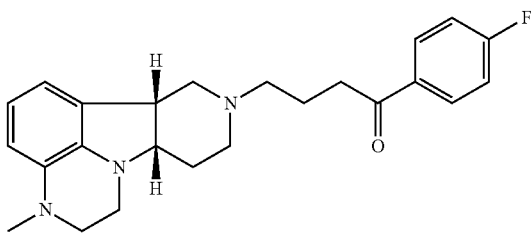 [SMILES: CN1CCN2c3c(cccc31)[C@@H]1CN(CCCC(=O)c3ccc(F)cc3)CC[C@@H]12]

ITI-007 is a potent 5-HT2A receptor ligand (Ki=0.5 nM) with strong affinity for dopamine (DA) D2 receptors (Ki=32 nM) and the serotonin transporter (SERT) (Ki=62 nM) but negligible binding to receptors (e.g., H1 histaminergic, 5-HT2C, and muscarinic) associated with cognitive and metabolic side effects of antipsychotic drugs. ITI-007 is currently in clinical trials, i.e., for treatment of schizophrenia. While ITI-007 is a promising drug, its production and formulation present challenges. In free base form, ITI-007 is an oily, sticky solid, with poor aqueous solubility. Making salts of the compound has proven to be unusually difficult. A hydrochloride salt form of ITI-007 was disclosed in U.S. Pat. No. 7,183,282, but this particular salt form was hygroscopic and showed poor stability. It was obtained by precipitation from diethyl ether. A toluenesulfonic acid addition salt (tosylate) of ITI-007 was finally identified and described in WO 2009/114181, and its equivalent US 2011/112105, the contents of each of which are hereby incorporated by reference in their entireties.

There is a need for alternative stable and pharmaceutically acceptable salts and polymorphs of ITI-007.

SUMMARY

In an effort to find new salts and polymorphs of ITI-007, an extensive salt screen was undertaken. ITI-007 does not readily form salts with other common, pharmaceutically acceptable acids, despite the good solubility of the free base in a variety of organic solvents. Eventually, a toluenesulfonic acid addition salt (tosylate) was prepared, as described in WO 2009/114181 and US 2011/112105, but no other stable salts were found. Finally, a major salt screen was carried out, wherein the free base compound was studied in different solvent systems and under different conditions, and then systematically screened using a selection of over 100 acids under different conditions and with different solvent, co-solvent and anti-solvent systems, to identify possible salt forms. Following extensive screening and experimentation, three new hydrochloride polymorphs were discovered. These hydrochloride salt forms are crystalline and stable.

The disclosure thus provides new hydrochloride salt forms of ITI-007, which are especially advantageous for use in the preparation of galenic formulations, together with methods of making and using the same.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
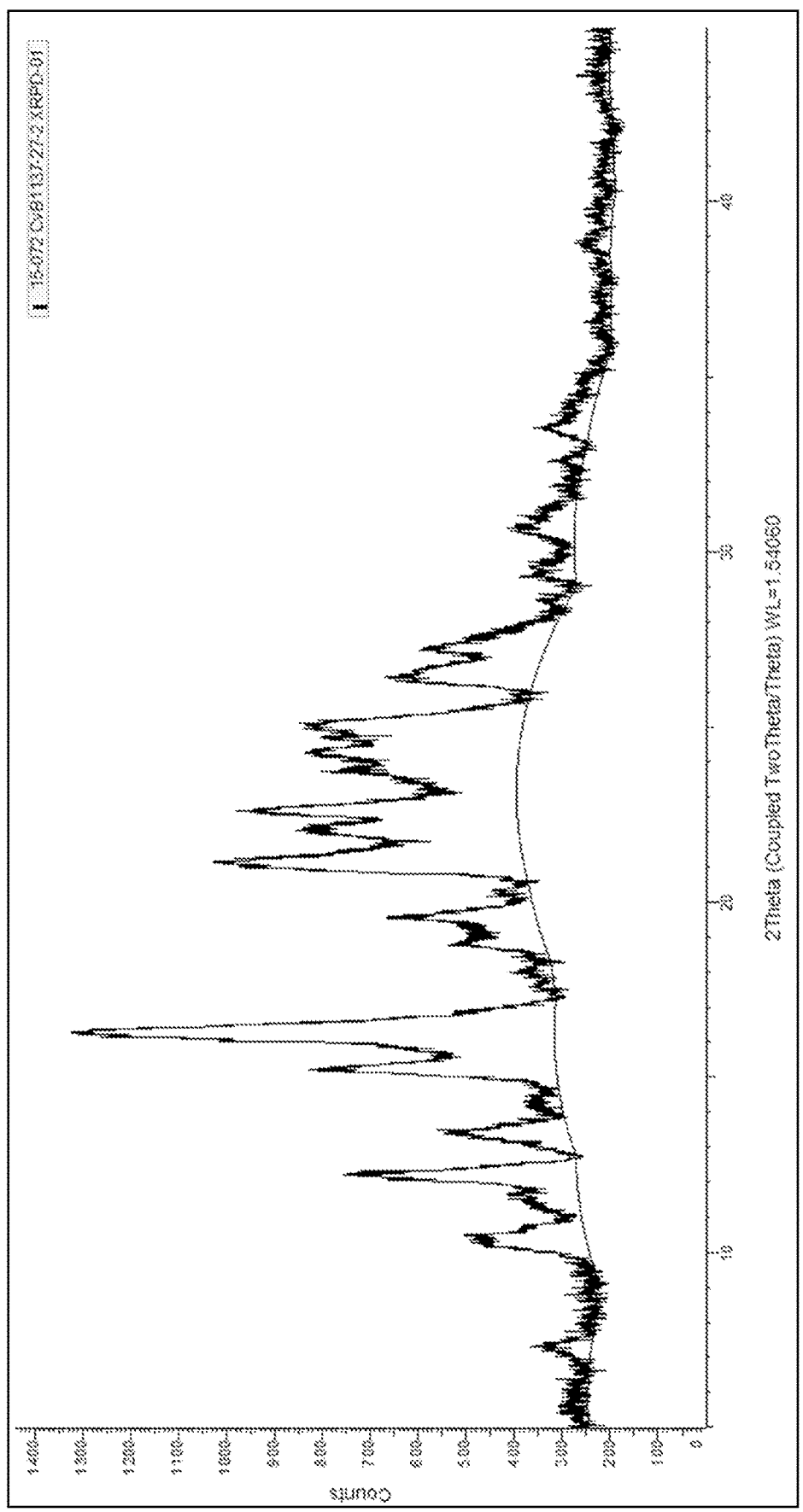
FIG. 1 depicts an X-ray powder diffraction pattern for an ITI-007 hydrochloride salt crystal (Polymorph 1).

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In a first embodiment, the invention provides 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in stable hydrochloride salt form (Salt 1). The invention therefore provides the following:

1.1. Salt 1 in solid form.
1.2. Salt 1 or 1.1 in crystalline form, e.g., dry crystalline form.
1.3. Salt 1.2 in a homogeneous crystal form, free or substantially free of other forms, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. %, of amorphous forms.
1.4. Any foregoing form of Salt 1 in crystalline form, when crystallized from a mixture of hydrochloric acid and ITI-007, e.g. in an organic solvent, e.g., comprising toluene, ethyl acetate, cyclopropylmethyl ether (CPME), acetonitrile, 1-butanol, or mixtures thereof; e.g., wherein the hydrochloric acid and ITI-007 are in a molar ratio of about 1:1 or about 1:2.
1.5. Any foregoing form of Salt 1 which is a solvate, e.g., an ethyl acetate solvate, or a toluene solvate, or a CPME solvate, or a 1-butanol solvate.
1.6. Any foregoing form of Salt 1 which is not a solvate.
1.7. Any foregoing form of Salt 1 which is a hydrate.
1.8. Any foregoing form of Salt 1 which is not a hydrate.
1.9. Any foregoing form of Salt 1 formed by combining free ITI-007 free base and hydrochloric acid in a molar ratio from 1:1 to 1:2, e.g., a 1:1 molar ratio or a 1:2 molar ratio.
1.10. Any foregoing form of Salt 1, wherein the salt is formed from a slurry experiment in ethyl acetate to yield Polymorph 1, e.g., using a 1:1 molar ratio of ITI-007 free base to hydrochloride acid in CPME
1.11. Salt 1.10, wherein a DSC analysis shows two endothermic events, at 117° C. and 228° C., e.g. wherein a DSC/TGA analysis shows the first endothermic event at $T_{onset}$=110° C., $T_{peak}$=117° C. and ΔE=−15 J/g, and the second event at $T_{onset}$=218° C., $T_{peak}$=228° C. and ΔE=−39 J/g.
1.12. Salt 1.10 or 1.11, in the form of a crystal having an X-ray powder diffraction pattern corresponding to the d-spacing and/or angle (2-theta) values of the following table, for example at least five, or at least six, or at least seven, or at least eight of said values, e.g., taking into account potential variations due to sample purity and instrument variation, for example 2 θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, e.g., at least 0.5, e.g., at least 0.6, e.g., comprising peaks 1, 2, 6, 7, 8, and 9:

| XRPD (Cu anode, Ni filter) for Hydrochloride Salt Crystal Polymorph 1 | | | |
|---|---|---|---|
| # | Angle | d Value | Rel. Intensity |
| 1 | 7.28967 | 12.11707 | 0.086731 |
| 2 | 10.2809 | 8.59734 | 0.200258 |
| 3 | 10.442 | 8.465061 | 0.200747 |
| 4 | 12.21318 | 7.241127 | 0.433615 |
| 5 | 13.42102 | 6.592047 | 0.224916 |
| 6 | 15.23882 | 5.809543 | 0.438444 |
| 7 | 16.28812 | 5.437572 | 1 |
| 8 | 16.80838 | 5.27042 | 0.215476 |
| 9 | 18.82491 | 4.710149 | 0.181319 |
| 10 | 19.56592 | 4.533406 | 0.249163 |
| 11 | 21.14059 | 4.199153 | 0.652782 |
| 12 | 22.06027 | 4.026127 | 0.400921 |
| 13 | 22.07126 | 4.024148 | 0.42148 |
| 14 | 22.62619 | 3.926692 | 0.559073 |
| 15 | 23.78436 | 3.738039 | 0.298317 |
| 16 | 24.30932 | 3.658491 | 0.445871 |
| 17 | 25.02641 | 3.555265 | 0.440086 |
| 18 | 26.3953 | 3.373907 | 0.26406 |
| 19 | 26.44407 | 3.367795 | 0.277233 |
| 20 | 26.5014 | 3.360641 | 0.252958 |
| 21 | 27.23728 | 3.271492 | 0.230046 |
| 22 | 29.35735 | 3.039883 | 0.073715 |
| 23 | 33.52987 | 2.670518 | 0.091379 |

1.13. Any form of Salt 1.10-1.12, in the form of a crystal having an X-ray powder diffraction pattern corresponding to FIG. 1, e.g., taking into account potential variations due to sample purity and instrument variation, for example 2 θ shifts due to variation in X-ray wavelength, e.g., an X-ray powder diffraction pattern corresponding to FIG. 1 generated using an X-ray diffractometer with a copper anode and a nickel filter.
1.14. Any form of Salt 1.10-1.13, in the form of a crystal having an X-ray powder diffraction pattern having at least 5, or at least 6, or at least 7, or at least 8, peaks having angle (2-theta) values selected from the group consisting of about 7.29, 10.28, 10.44, 12.21, 13.42, 15.24, 16.29, 16.81, 18.82, 19.57, 21.14, 22.06, 22.07, 22.63, 23.78, 24.31, 25.03, 26.40, 26.44, 26.50, 27.24, 29.36, and 33.53, taking into account potential variations due to sample purity and instrument variation, wherein the X-ray powder diffraction pattern is generated using an X-ray diffractometer with a copper anode and a nickel filter.
1.15. Any form of Salt 1.10-1.14, in the form of a crystal having an X-ray powder diffraction pattern having at least 5, or at least 6, or at least 7, or at least 8, peaks having d-spacing values selected from the group consisting of about 12.12, 8.60, 8.47, 7.24, 6.59, 5.81, 5.44, 5.27, 4.71, 4.53, 4.20, 4.03, 4.02, 3.93, 3.74, 3.66, 3.56, 3.37, 3.37, 3.36, 3.27, 3.04, and 2.67, taking into account potential variations due to sample purity and instrument variation, wherein the X-ray powder diffraction pattern is generated using an X-ray diffractometer with a copper anode and a nickel filter.
1.16. Any form of Salt 1.10-1.15, in the form of a crystal having an X-ray powder diffraction pattern having at least 5, or at least 6, or at least 7, or at least 8, peaks having angle (2-theta) values and/or d-spacing values as provided in 1.14 and 1.15.
1.17. Any form of Salt 1.10-1.16, in the form of a crystal having an X-ray powder diffraction powder having relative angle (2-theta) values as provided in the table of embodiment 1.12, wherein the values are shifted by up to +/−0.2 degrees, e.g., wherein the values are substantially uniformly shifted by up to +/−0.2 degrees.
1.18. Any form of Salt 1 or 1.1-1.9, wherein the salt is formed from a slurry experiment in toluene to yield Polymorph 2, e.g., using a 1:1 molar ratio of ITI-007 free base to hydrochloride acid in CPME.
1.19. Salt 1.18, wherein a DSC analysis shows two endothermic events, at 121° C. and 228° C., e.g. wherein a DSC/TGA analysis shows a first endothermic event at $T_{onset}$=108° C., $T_{peak}$=121° C. and ΔE=−23 J/g, and the second event at $T_{onset}$=215° C., $T_{peak}$=228° C. and ΔE=−57 J/g.

1.20. Salt 1.18 or 1.19, in the form of a crystal having an X-ray powder diffraction pattern corresponding to the d-spacing and/or angle (2-theta) values of the following table, for example at least five, or at least six, or at least seven, or at least eight of said values, e.g., taking into account potential variations due to sample purity and instrument variation, for example 2 θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, e.g., at least 0.5, e.g., at least 0.6, e.g., comprising peaks 1, 2, 6, 7, 8, and 9:

| XRPD (Cu anode, Ni filter) for Hydrochloride Salt Crystal Polymorph 2 | | | |
|---|---|---|---|
| # | Angle | d Value | Rel. Intensity |
| 1 | 10.51587 | 8.405758 | 0.510923 |
| 2 | 11.72088 | 7.54414 | 0.189459 |
| 3 | 12.09875 | 7.309357 | 0.796857 |
| 4 | 13.11974 | 6.74274 | 0.311634 |
| 5 | 14.24802 | 6.21123 | 0.24302 |
| 6 | 16.03021 | 5.524469 | 0.999989 |
| 7 | 16.56551 | 5.347139 | 0.83136 |
| 8 | 16.6931 | 5.306556 | 0.7834 |
| 9 | 18.93689 | 4.682549 | 0.251913 |
| 10 | 19.84092 | 4.471187 | 0.162883 |
| 11 | 21.09046 | 4.209022 | 0.703611 |
| 12 | 20.84009 | 4.25902 | 0.269821 |
| 13 | 21.77743 | 4.077775 | 0.750891 |
| 14 | 22.29105 | 3.984963 | 1 |
| 15 | 22.46965 | 3.953692 | 0.838087 |
| 16 | 24.20198 | 3.674474 | 0.667304 |
| 17 | 24.61919 | 3.61314 | 0.846243 |
| 18 | 26.8244 | 3.320902 | 0.36495 |
| 19 | 28.28183 | 3.152993 | 0.182531 |

1.21. Any form of Salt 1.18-1.20, in the form of a crystal having an X-ray powder diffraction pattern corresponding to FIG. 2, e.g., taking into account potential variations due to sample purity and instrument variation, for example 2 θ shifts due to variation in X-ray wavelength, e.g., an X-ray powder diffraction pattern corresponding to FIG. 2 generated using an X-ray diffractometer with a copper anode and a nickel filter.

1.22. Any form of Salt 1.18-1.21, in the form of a crystal having an X-ray powder diffraction pattern having at least 5, or at least 6, or at least 7, or at least 8, peaks having angle (2-theta) values selected from the group consisting of about 10.52, 11.72, 12.10, 13.12, 14.25, 16.03, 16.57, 16.69, 18.94, 19.84, 21.09, 20.84, 21.78, 22.29, 22.47, 23.20, 24.62, 26.82, and 28.28, taking into account potential variations due to sample purity and instrument variation, wherein the X-ray powder diffraction pattern is generated using an X-ray diffractometer with a copper anode and a nickel filter.

1.23. Any form of Salt 1.18-1.22, in the form of a crystal having an X-ray powder diffraction pattern having at least 5, or at least 6, or at least 7, or at least 8, peaks having d-spacing values selected from the group consisting of about 8.41, 7.54, 7.31, 6.74, 6.21, 5.52, 5.35, 5.31, 4.68, 4.47, 4.21, 4.26, 4.08, 3.98, 3.95, 3.67, 3.61, 3.32, and 3.15, taking into account potential variations due to sample purity and instrument variation, wherein the X-ray powder diffraction pattern is generated using an X-ray diffractometer with a copper anode and a nickel filter.

1.24. Any form of Salt 1.18-1.23, in the form of a crystal having an X-ray powder diffraction pattern having at least 5, or at least 6, or at least 7, or at least 8, peaks having angle (2-theta) values and/or d-spacing values as provided in 1.22 and 1.23.

1.25. Any form of Salt 1.18-1.24, in the form of a crystal having an X-ray powder diffraction powder having relative angle (2-theta) values as provided in the table of embodiment 1.20, wherein the values are shifted by up to +/−0.2 degrees, e.g., wherein the values are substantially uniformly shifted by up to +/−0.2 degrees.

1.26. Any form of Salt 1 or 1.1-1.9, wherein the salt is formed from a slurry experiment in CPME to yield Polymorph 3, e.g., using a 1:1 molar ratio of ITI-007 free base to hydrochloride acid in CPME.

1.27. Salt 1.26, wherein a DSC analysis shows two endothermic events, at 122° C. and 209° C., e.g. wherein a DSC/TGA analysis shows a first endothermic event at $T_{onset}$=97° C., $T_{peak}$=122° C. and ΔE=−38 J/g, and the second event at $T_{onset}$=192° C., $T_{peak}$=209° C. and ΔE=−13 J/g.

1.28. Salt 1.26 or 1.27, in the form of a crystal having an X-ray powder diffraction pattern corresponding to the d-spacing and/or angle (2-theta) values of the following table, for example at least five, or at least six, or at least seven, or at least eight of said values, e.g., taking into account potential variations due to sample purity and instrument variation, for example 2 θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, e.g., at least 0.5, e.g., at least 0.6, e.g., comprising peaks 1, 2, 6, 7, 8, and 9:

| XRPD (Cu anode, Ni filter) for Hydrochloride Salt Crystal Polymorph 3 | | | |
|---|---|---|---|
| # | Angle | d Value | Rel. Intensity |
| 1 | 6.113585 | 14.44517 | 0.204101 |
| 2 | 10.09204 | 8.757802 | 0.489434 |
| 3 | 10.35476 | 8.536179 | 0.605859 |
| 4 | 11.54239 | 7.660397 | 0.585963 |
| 5 | 12.08467 | 7.317844 | 1 |
| 6 | 12.93047 | 6.841012 | 0.161332 |
| 7 | 13.23207 | 6.685754 | 0.254659 |
| 8 | 15.77195 | 5.614344 | 0.712069 |
| 9 | 18.19631 | 4.871422 | 0.250223 |
| 10 | 19.51964 | 4.544048 | 0.326853 |
| 11 | 20.92257 | 4.242415 | 0.744994 |
| 12 | 23.86984 | 3.724845 | 0.732022 |
| 13 | 24.96878 | 3.563339 | 0.326213 |
| 14 | 26.39552 | 3.373879 | 0.575626 |

1.29. Any form of Salt 1.26-1.28, in the form of a crystal having an X-ray powder diffraction pattern corresponding to FIG. 3, e.g., taking into account potential variations due to sample purity and instrument variation, for example 2 θ shifts due to variation in X-ray wavelength, e.g., an X-ray powder diffraction pattern corresponding to FIG. 3 generated using an X-ray diffractometer with a copper anode and a nickel filter.

1.30. Any form of Salt 1.26-1.29, in the form of a crystal having an X-ray powder diffraction pattern having at least 5, or at least 6, or at least 7, or at least 8, peaks having angle (2-theta) values selected from the group consisting of about 6.11, 10.09, 10.35, 11.54, 12.08, 12.93, 13.23, 15.77, 18.20, 19.52, 20.92, 23.87, 24.97, and 26.40, taking into account potential variations due to sample purity and instrument variation, wherein the X-ray powder diffraction pattern is generated using an X-ray diffractometer with a copper anode and a nickel filter.

1.31. Any form of Salt 1.26-1.30, in the form of a crystal having an X-ray powder diffraction pattern having at least 5, or at least 6, or at least 7, or at least 8, peaks having d-spacing values selected from the group consisting of about 14.45, 8.76, 8.54, 7.66, 7.32, 6.84, 6.69, 5.61, 4.87, 4.54, 4.24, 3.73, 3.56, and 3.37, taking into account potential variations due to sample purity and instrument variation, wherein the X-ray powder diffraction pattern is generated using an X-ray diffractometer with a copper anode and a nickel filter.

1.32. Any form of Salt 1.26-1.31, in the form of a crystal having an X-ray powder diffraction pattern having at least 5, or at least 6, or at least 7, or at least 8, peaks having angle (2-theta) values and/or d-spacing values as provided in 1.30 and 1.31.

1.33. Any form of Salt 1.26-1.32, in the form of a crystal having an X-ray powder diffraction powder having relative angle (2-theta) values as provided in the table of embodiment 1.28, wherein the values are shifted by up to +/−0.2 degrees, e.g., wherein the values are substantially uniformly shifted by up to +/−0.2 degrees.

1.34. Any foregoing form of Salt 1 wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule; for example, any foregoing form of Salt 1 wherein the —CH$_2$— adjacent to the methylated nitrogen moiety and/or adjacent to the carbonyl moiety of ITI-007 is deuterated, e.g., is in the form of —CHD- or —CD$_2$- at levels which are significantly higher than the natural deuterium:protium isotope ratio or the deuterium:protium isotope ratio at other positions in the molecule, and/or wherein the methyl group is deuterated, e.g., is CD$_3$-, e.g., at levels which are significantly higher than the natural deuterium:protium isotope ratio or the deuterium:protium isotope ratio at other positions in the molecule, e.g., as described in WO 2015/154025, the contents of which are incorporated herein by reference.

1.35. Any foregoing form of Salt 1 exhibiting any combination of characteristics as described in 1.1-1.34.

In another embodiment, the invention provides a process (Process 1) for the production of Salt 1, comprising
(a) reacting 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with hydrochloric acid, e.g., together with an organic solvent (e.g., comprising toluene, ethyl acetate, CPME, acetonitrile, 1-butanol, or mixtures thereof), for example, wherein the hydrochloric acid and ITI-007 are in a molar ratio of from 1:1 to 1:2, or about 1:1, or about 1:2; and
(b) recovering the hydrochloride salt thus formed, e.g., recovering a salt according to any of Salt 1, et seq. above.

In an embodiment of Process 1, the hydrochloric acid is provided as a gas (hydrogen chloride), or as an aqueous solution, or as a solution in an organic solvent, e.g., selected from methanol, ethanol, isopropanol, cyclopropylmethyl ether (CPME), diethyl ether, 1,4-dioxane, or any mixture thereof.

In another embodiment of Process 1, the reaction step (a) comprises dissolving or suspending the ITI-007 free base in an organic solvent, e.g., selected from toluene, ethyl acetate, CPME, acetonitrile, 1-butanol, or mixtures thereof, and adding thereto the hydrochloric acid. In another embodiment of Process 1, the reaction step (a) comprises combining the ITI-007 free base with the hydrochloric acid and adding thereto an organic solvent, e.g., selected from toluene, ethyl acetate, CPME, acetonitrile, 1-butanol, or mixtures thereof.

In some embodiments of Process 1, the process step (a) is carried out as a batch process, and in other embodiments the process step (a) is carried out as a continuous (flow) process.

In another embodiment, the invention provides a method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising reacting a crude solution of ITI-007 with hydrochloric acid, and recovering the hydrochloride salt thus formed, e.g., in accordance with Process 1, and optionally converting the hydrochloride salt back to ITI-007 free base or to another salt form.

In another embodiment, the invention provides the use of hydrochloric acid in a method of isolating and/or purifying ITI-007.

As used herein, "hydrochloric acid" refers pure (gaseous) hydrogen chloride, hydrochloric acid in water (aqueous hydrochloric acid), or hydrochloric acid in an organic solvent (i.e., hydrogen chloride in an organic solvent), wherein the organic solvent may be selected from any suitable organic solvent capable of dissolving hydrogen chloride, such as, methanol, ethanol, isopropanol, cyclopropylmethyl ether (CPME), diethyl ether, 1,4-dioxane, or any mixture thereof.

In another embodiment, the invention provides a pharmaceutical composition comprising Salt 1, e.g., any of Salt 1.1-1.35, as active ingredient, in combination or association with a pharmaceutically acceptable diluent or carrier.

In another embodiment, the invention provides pharmaceutical composition comprising Salt 1, e.g., any of Salt 1.1-1.35, as active ingredient, in combination or association with a pharmaceutically acceptable diluent or carrier, wherein the Salt 1 is predominantly, or is entirely or substantially entirely, in dry crystalline form.

In a particular embodiment, the invention provides a pharmaceutical composition comprising Salt 1, e.g., any of Salt 1.1-1.35, as active ingredient, in combination or association with a pharmaceutically acceptable diluent or carrier, in the form of an injectable depot form, to provide extended release of ITI-007.

In another embodiment, the invention provides Salt 1, e.g., any of Salt 1.1-1.35, or a pharmaceutical composition comprising Salt 1, e.g., any of Salt 1.1-1.35, for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the 5-$HT_{2A}$ receptor, serotonin transporter (SERT), and/or dopamine $D_1/D_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of any of Salt 1, et seq.

EXAMPLES

The following equipment and methods are used to isolate and characterize the exemplified salt forms:

X-Ray Powder Diffraction (XRPD):

The X-ray powder diffraction studies are performed using a Bruker AXS D2 PHASER in Bragg-Brentano configuration, equipment #1549/#2353. The equipment uses a Cu anode at 30 kV, 10 mA; sample stage standard rotating; monochromatization by a Kβ-filter (0.5% Ni). Slits: fixed divergence slits 1.0 mm)(=0.61°, primary axial Soller slit 2.5°, secondary axial Soller slit 2.5°. Detector: Linear detector LYNXEYE with receiving slit 5° detector opening. The standard sample holder (0.1 mm cavity in (510) silicon wafer) has a minimal contribution to the background signal. Measurement conditions: scan range 5-45° 2θ, sample rotation 5 rpm, 0.5 s/step, 0.010°/step, 3.0 mm detector slit; and all measuring conditions are logged in the instrument control file. As system suitability, corundum sample A26-B26-S (NIST standard) is measured daily. The software used for data collection is Diffrac.Commander v2.0.26. Data analysis is done using Diffrac.Eva v1.4. No background correction or smoothing is applied to the patterns.

Simultaneous Thermogravimetry (TGA) and Differential Scanning Calorimetry (DSC) or TGA/DSC Analysis:

The TGA/DSC studies are performed using a Mettler Toledo TGA/DSC1 Stare System, equipment #1547, autosampler equipped, using pin-holed Al-crucibles of 40 μl. Measurement conditions: 5 min 30.0° C., 30.0-350.0° C. with 10° C./min., N2 flow of 40 ml/min. The software used for instrument control and data analysis is STARe v12.10.

Differential Scanning Calorimetry (DSC):

The DSC studies are performed using a Mettler Toledo DSC1 STARe System, equipment #1564. The samples are made using Al crucibles (40 μl; pierced). Typically 1-8 mg of sample is loaded onto a pre-weighed Al crucible and is kept at 30° C. for 5 minutes, after which it is heated at 10° C./min from 30° C. to 350° C. and kept at 350° C. for 1 minute. A nitrogen purge of 40 ml/min is maintained over the sample. As system suitability check Indium and Zinc are used as references. The software used for data collection and evaluation is STARe Software v12.10 build 5937. No corrections are applied to the thermogram.

Polarized Light Microscopy (PLM):

The microscopy studies are performed using an AxioVert 35M, equipped with an AxioCamERc 5s, equipment #1612. The microscope is equipped with four lenses: Zeiss A-Plan 5x/0.12, Zeiss A-Plan 10x/0.25, LD A-Plan 20x/0.30 and Achros TIGMAT 32x/0.40. Data collection and evaluation is performed using Carl Zeiss Zen AxioVision Blue Edition Lite 2011 v1.0.0.0 software. A small amount of sample is loaded on an object glass and carefully spread until a thin layer is obtained.

Dynamic Vapour Sorption (DVS):

The Dynamic Vapour Sorption studies are performed using a Surface Measurement Systems Ltd. DVS-1 No Video, equipment #2126. The sample is loaded into a balance pan, typically 20-30 mg, and equilibrated at 0% RH. After the material was dried, the RH is increased with 10% per step for 1 hour per increment, ending at 95% RH. After completion of the sorption cycle, the sample was dried using the same method. The software used for data collection is DVSWin v3.01 No Video. Data analysis is performed using DVS Standard Analysis Suite v6.3.0 (Standard).

Particle Size Distribution (PSD):

The particle size distribution studies are performed using a Malvern Instruments Mastersizer, equipment #1712. The Mastersizer uses a 300RF lens range of 0.05 μm-900 mm. Polydisperse is used as analysis model. Measurement conditions: before each sample measurement a background measurement is performed, the background scan time is 12 seconds (12000 snaps). Each sample is dispersed in Multipar G, refractive index of 1.42. The obscuration range on sample dispersion is between 10%-30%. Each sample is measured 6 times at t=0 and t=30 minutes and the measurement scan time is 10 seconds (10000 snaps). The targeted stirring speed of the sample dispersion unit is 2000±10 rpm. Data collection and evaluation is performed using Mastersizer S Version 2.19 software.

Capillary Melting Point:

The capillary melting point is determined on a Büchi Melting Point B-545, equipment #000011, conform USP guidelines.

X-Ray Fluorescence (XRF):

The X-ray fluorescence studies are performed using a Bruker AXS S2 RANGER, equipment #2006. Using an end-window X-ray tube with Palladium anode and an ultrathin Beryllium window (75 μm) for superior light element analysis. As detector the Xflash V5 detector with Cr, Ti, Al, Ta collimator (energy resolution <129 eV FWHM at 100 000 cps Mnkα) is used. The S2 Ranger is equipped with an autosampler with integrated 28 position X-Y automatic sample changer with exchangeable tray, which allows maximum sample diameter of 40 mm. Samples are mounted in steel rings of 51.5 mm diameter for automatic operation. Measurement conditions: disposable liquid cups (35 mm inner diameter, 40 mm outer diameter) with polypropylene foil 5 μm. As system suitability check a copper disk is measured daily and a glass disk, containing several elements, is measured weekly. The software used for data collection is S2 Ranger Control Software V4.1.0. Data analysis is performed using SPECTRA EDX V2.4.3 evaluation software. No background correction or smoothing is applied to the patterns.

Fourier Transform Infrared Spectroscopy (FT-IR):

The FT-IR studies are performed using a Thermo Scientific Nicolet iS50, equipment #2357. An attenuated total reflectance (ATR) technique was used with a beam splitter of KBr. Experiment setup of the collected sample is used number of scans 16 with a resolution of 4 from 400 $cm^{-1}$ to 4000 $cm^{-1}$. The software OMNIC version 9.2 is used for data collection and evaluation.

Thermogravimetric Analysis (TGA) with Infrared Spectroscopy (TGA-IR):

In TGA-IR, the off-gassing materials are directed through a transfer line to a gas cell, where the infrared light interacts with the gases. The temperature ramp and first derivative weight loss information from the TGA is shown as a Gram-Schmidt (GS) profile; the GS profile essentially shows the total change in the IR signal relative to the initial state. In most cases, the GS and the derivative weight loss will be similar in shape, although the intensity of the two can differ. For this experiment are two devices coupled to each other. The TGA studies are performed using a Mettler Toledo TGA/DSC1 STARe System with a 34-position auto sampler, equipment #1547. The samples are made using Al crucibles (100 μl; pierced). Typically 20-50 mg of sample is loaded into a pre-weighed Al crucible and is kept at 30° C. for 5 minutes after which it is heated at 10° C./min from 30° C. to 350° C. A nitrogen purge of 40 ml/min is maintained over the sample. The TGA-IR module of the Nicolet iS50 is coupled to the TGA/DSC1. The IR studies were performed using a Thermo Scientific Nicolet iS50, equipment #2357. Experiment setup of the collected series, the profile Gram-Schmidt is used number of scans 10 with a resolution of 4. The software OMNIC version 9.2 is used for data collection and evaluation.

High Performance Liquid Chromatography (HPLC):

The high performance liquid chromatography analyses are performed on LC-31, equipped with an Agilent 1100 series G1322A degasser equipment #1894, an Agilent 1100 series G1311A quaternary pump equipment #1895, an Agilent 1100 series G1313A ALS equipment #1896, an Agilent 1100 series G1318A column equipment #1897 and an Agilent 1100 series G1314A VWD equipment #1898/LC-34, equipped with an Agilent 1200 series G1379B degasser equipment #2254, an Agilent 1100 series G1311A quaternary pump equipment #2255, Agilent 1100 series G1367A WPALS equipment #1656, an Agilent 1100 series G1316A column equipment #2257 and an Agilent 1100 series G1315B DAD equipment #2258. Data is collected and evaluated using Agilent ChemStation for LC systems Rev. B.04.02[96]. Solutions are prepared as follows: Mobile phase A: Add 800 ml of MilliQ water to a 1 L volumetric flask. Add 1 ml of TFA and homogenize. Fill up to the mark with MilliQ; Mobile phase B: Add 800 ml of Acetonitrile to a 1 L volumetric flask. Add 1 ml of TFA and homogenize. Fill up to the mark with Acetonitrile; Diluent: 50/50 MeOH/ACN.

Example 1: Salt Crystal Screen

Solubility of ITI-007 free base in various solvents is evaluated, and based on the results of the solubility range, suitable solvents are selected for the salt screen. The salt screen is divided into seven separate screens, using 90 different counterions, six different solvents, and including four different crystallization methods (slurry crystallization, cooling crystallization, evaporation and precipitation). The counterions are selected based upon availability and potential suitability to form pharmaceutically acceptable acid addition salts. They include the class I, II and III acids identified in Stahl P. H., Wermuch C. G. (editors), Handbook of Pharmaceutical Salts, IUPAC (2008). A total of 624 counterion/solvent/ratio variations are tested, and each of these is studied using each of the four crystallization methods. Of the 624 combinations tested, only nine combinations produce candidate crystalline salts: six hydrochloric acid conditions, and one condition each for oxalic acid, cyclamic acid and 4-aminosalicylic acid.

For the hydrochloric acid screens, both hydrochloric acid in CPME and hydrochloric acid in isopropanol are used. The molar ratio of free base to acid is 1:1 or 1:2. The reaction solvents screened include acetonitrile, methanol, isopropanol, ethyl acetate, toluene and CPME.

Candidate crystalline salts are observed for the following HCl conditions: (1) HCl/CPME in CPME solvent at a 1:1 molar ratio (slurry crystallization); (2) HCl/CPME in CPME solvent at a 1:2 molar ratio (slurry crystallization); (3) HCl/CPME in toluene solvent at a 1:2 molar ratio (slurry crystallization); (4) HCl/CPME in ethyl acetate solvent at a 1:2 molar ratio (slurry crystallization); (5) HCl/CPME in toluene solvent at a 1:1 molar ratio (cooling crystallization); and (6) HCl/isopropanol in ethyl acetate solvent at a 1:2 molar ratio (precipitation crystallization). The candidate crystalline salts are each obtained as powders, varying in color from yellow to grey. FT-IR analysis confirms these candidates to be salts, each showing approximately 70% similarity with the free base and showing HCl present. XRPD analysis confirms that each of these candidates are crystalline. LC-MS analysis confirms that there is no decomposition of the free base structure.

To confirm the formation of new hydrochloride salt crystals, scale-up experiments are conducted as follows.

Example 2: Hydrochloride Crystal Salt Polymorph 1

Approximately one gram of ITI-007 free base is added to ethyl acetate solvent at a concentration of 100 mg/mL. Hydrochloric acid in CPME solution is added to provide a 1:1 molar ratio of ITI-007 free base to HCl. The mixture is slurried at 50° C. overnight. The mixture is allowed to cool down to room temperature and is filtered and dried to give a yellow/brown solid. XRPD analysis shows the hydrochloride to be a crystalline solid. The XRPD pattern is shown in FIG. 1; the peaks are identified in tabular form in table 1:

TABLE 1

XRPD peak list
hydrochloride salt polymorph 1

| # | Angle | d Value | Rel. Intensity |
|---|---|---|---|
| 1 | 7.28967 | 12.11707 | 0.086731 |
| 2 | 10.2809 | 8.59734 | 0.200258 |
| 3 | 10.442 | 8.465061 | 0.200747 |
| 4 | 12.21318 | 7.241127 | 0.433615 |
| 5 | 13.42102 | 6.592047 | 0.224916 |
| 6 | 15.23882 | 5.809543 | 0.438444 |
| 7 | 16.28812 | 5.437572 | 1 |
| 8 | 16.80838 | 5.27042 | 0.215476 |
| 9 | 18.82491 | 4.710149 | 0.181319 |
| 10 | 19.56592 | 4.533406 | 0.249163 |
| 11 | 21.14059 | 4.199153 | 0.652782 |
| 12 | 22.06027 | 4.026127 | 0.400921 |
| 13 | 22.07126 | 4.024148 | 0.42148 |
| 14 | 22.62619 | 3.926692 | 0.559073 |
| 15 | 23.78436 | 3.738039 | 0.298317 |
| 16 | 24.30932 | 3.658491 | 0.445871 |
| 17 | 25.02641 | 3.555265 | 0.440086 |
| 18 | 26.3953 | 3.373907 | 0.26406 |
| 19 | 26.44407 | 3.367795 | 0.277233 |
| 20 | 26.5014 | 3.360641 | 0.252958 |
| 21 | 27.23728 | 3.271492 | 0.230046 |
| 22 | 29.35735 | 3.039883 | 0.073715 |
| 23 | 33.52987 | 2.670518 | 0.091379 |

The hydrochloride salt is also analyzed by DSC/TGA, DVS, HPLC, $^1$H-NMR and FT-IR. DSC/TGA analysis shows two endothermic events, the first endothermic event at $T_{onset}$=110° C., $T_{peak}$=117° C. and ΔE=−15 J/g, and the second event at $T_{onset}$=218° C., $T_{peak}$=228° C. and ΔE=−39 J/g. Both endothermic events are linked to a mass loss, of 4% and 13%, respectively. TGR-IR analysis shows these mass losses to be primarily ethyl acetate and water, indicating that an ethyl acetate solvate has formed. Analysis of the HPLC data shows a purity of 94% purity for this solvate. FT-IR analysis confirms the chemical structure. Dynamic vapor sorption (DVS) analysis shows some stepwise sorption; the total mass uptake at 95 RH % is 5%. This salt is thus moderately hygroscopic.

TABLE 2

Analytical results scale-up synthesis of the hydrochloride salt Polymorph 1

| Solvent | Appearance | DVS Hygroscopicity (%) | DSC ($T_{peak}$ °C.) | DVS: Mass loss (%) | HPLC purity (area %) |
|---|---|---|---|---|---|
| Ethyl acetate | Yellow/brown solid | 5 | 117 228 | 4 13 | 94 |

Example 3: Hydrochloride Crystal Salt Polymorph 2

Figure 2:
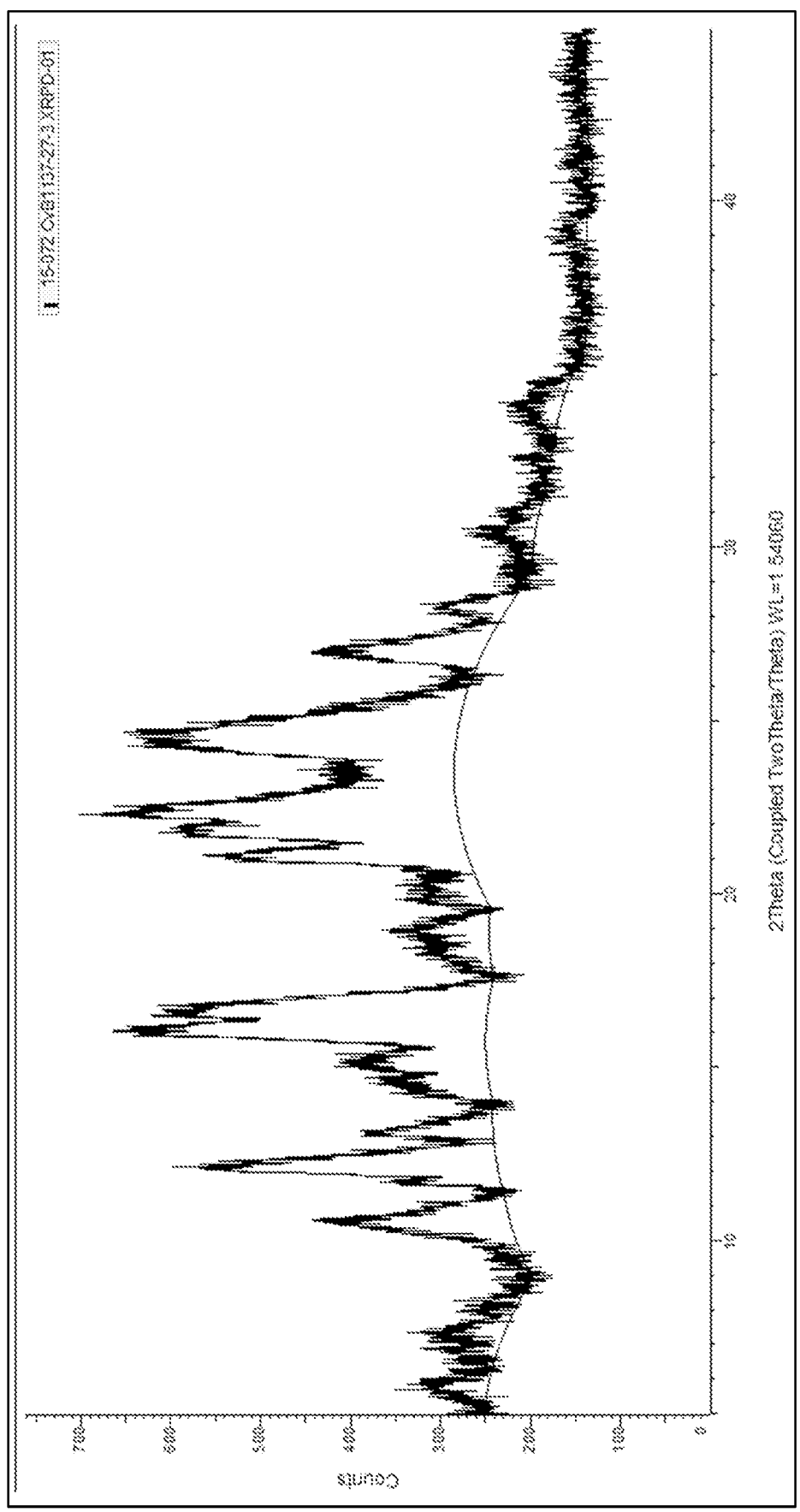
FIG. 2 depicts an X-ray powder diffraction pattern for an ITI-007 hydrochloride salt crystal (Polymorph 2).

Approximately one gram of ITI-007 free base is added to toluene solvent at a concentration of 100 mg/mL. Hydrochloric acid in CPME solution is added to provide a 1:1 molar ratio of ITI-007 free base to HCl. The mixture is slurried at 50° C. overnight. The mixture is allowed to cool down to room temperature and is filtered and dried to give a yellow/brown solid. XRPD analysis shows the hydrochloride to be a crystalline solid. The XRPD pattern is shown in FIG. 2; the peaks are identified in tabular form in table 3:

TABLE 3

XRPD peak list hydrochloride salt polymorph 2

| # | Angle | d Value | Rel. Intensity |
|---|---|---|---|
| 1 | 10.51587 | 8.405758 | 0.510923 |
| 2 | 11.72088 | 7.54414 | 0.189459 |
| 3 | 12.09875 | 7.309357 | 0.796857 |
| 4 | 13.11974 | 6.74274 | 0.311634 |
| 5 | 14.24802 | 6.21123 | 0.24302 |
| 6 | 16.03021 | 5.524469 | 0.999989 |
| 7 | 16.56551 | 5.347139 | 0.83136 |
| 8 | 16.6931 | 5.306556 | 0.7834 |
| 9 | 18.93689 | 4.682549 | 0.251913 |
| 10 | 19.84092 | 4.471187 | 0.162883 |
| 11 | 21.09046 | 4.209022 | 0.703611 |
| 12 | 20.84009 | 4.25902 | 0.269821 |
| 13 | 21.77743 | 4.077775 | 0.750891 |
| 14 | 22.29105 | 3.984963 | 1 |
| 15 | 22.46965 | 3.953692 | 0.838087 |
| 16 | 24.20198 | 3.674474 | 0.667304 |
| 17 | 24.61919 | 3.61314 | 0.846243 |
| 18 | 26.8244 | 3.320902 | 0.36495 |
| 19 | 28.28183 | 3.152993 | 0.182531 |

The hydrochloride salt is analyzed by DVS, DSC/TGA and HPLC, and the results are summarized in table 4. DSC/TGA analysis shows two endothermic events, the first at $T_{onset}$=108° C., $T_{peak}$=121° C. and $\Delta E$=−23 J/g, and the second at $T_{onset}$=215° C., $T_{peak}$=228° C. and $\Delta E$=−57 J/g. Both endothermic events are linked to a mass loss, of 4% and 13%, respectively. TGR-IR analysis shows these mass losses to be primarily toluene and water, indicating that a toluene solvate has formed. Analysis of the HPLC data shows a purity of 90% purity for this solvate. FT-IR analysis confirms the chemical structure. Dynamic vapor sorption (DVS) analysis shows some stepwise sorption; the total mass uptake at 95 RH % is 12%. This salt is thus moderately hygroscopic.

TABLE 4

Analytical results scale-up synthesis of the hydrochloride salt polymorph 2

| Solvent | Appearance | DVS Hygroscopicity (%) | DSC ($T_{peak}$ °C.) | Mass loss (%) | HPLC purity (area %) |
|---|---|---|---|---|---|
| Toluene | Yellow/brown solid | 12 | 121 228 | 4 13 | 90 |

Example 4: Hydrochloride Crystal Salt Polymorph 3

Figure 3:
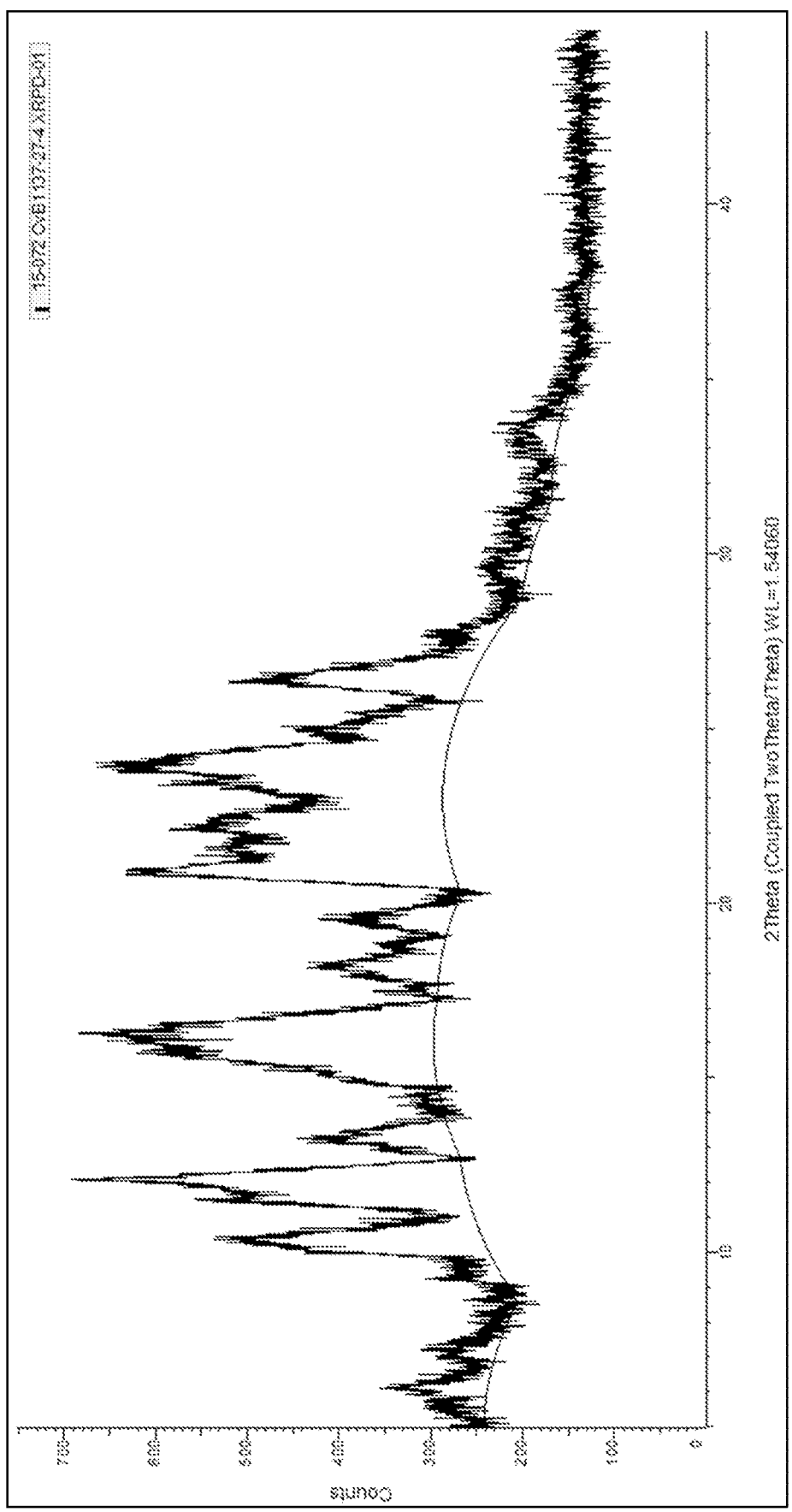
FIG. 3 depicts an X-ray powder diffraction pattern for an ITI-007 hydrochloride salt crystal (Polymorph 3).

Approximately one gram of ITI-007 free base is added to CPME solvent at a concentration of 100 mg/mL. Hydrochloric acid in CPME solution is added to provide a 1:1 molar ratio of ITI-007 free base to HCl. The mixture is slurried at 50° C. overnight. The mixture is allowed to cool down to room temperature and is filtered and dried to give an off-white powdery solid. XRPD analysis shows the hydrochloride to be a crystalline solid. The XRPD pattern is shown in FIG. 3; the peaks are identified in tabular form in table 5:

TABLE 5

XRPD peak list of the cyclamate salt

| # | Angle | d Value | Rel. Intensity |
|---|---|---|---|
| 1 | 6.113585 | 14.44517 | 0.204101 |
| 2 | 10.09204 | 8.757802 | 0.489434 |
| 3 | 10.35476 | 8.536179 | 0.605859 |
| 4 | 11.54239 | 7.660397 | 0.585963 |
| 5 | 12.08467 | 7.317844 | 1 |
| 6 | 12.93047 | 6.841012 | 0.161332 |
| 7 | 13.23207 | 6.685754 | 0.254659 |
| 8 | 15.77195 | 5.614344 | 0.712069 |
| 9 | 18.19631 | 4.871422 | 0.250223 |
| 10 | 19.51964 | 4.544048 | 0.326853 |
| 11 | 20.92257 | 4.242415 | 0.744994 |
| 12 | 23.86984 | 3.724845 | 0.732022 |
| 13 | 24.96878 | 3.563339 | 0.326213 |
| 14 | 26.39552 | 3.373879 | 0.575626 |

The hydrochloride salt is analyzed by DVS, DSC/TGA and HPLC. The results are summarized in table 6. DSC/TGA analysis shows two endothermic events, the first at $T_{onset}$=97° C., $T_{peak}$=122° C. and $\Delta E$=−38 J/g, and the second event at $T_{onset}$=192° C., $T_{peak}$=209° C. and $\Delta E$=−13 J/g. Both endothermic events are linked to a mass loss, of 7% and 13%, respectively. TGR-IR analysis shows these mass losses to be primarily CPME and water, indicating that a CPME solvate has formed. Analysis of the HPLC data shows a purity of 80% purity for this solvate. FT-IR analysis confirms the chemical structure. Dynamic vapor sorption (DVS) analysis shows some stepwise sorption; the total mass uptake at 95 RH % is 10%. This salt is thus moderately hygroscopic.

TABLE 6

Analytical results scale-up synthesis
of the hydrochloride salt Polymorph 3.

| Solvent | Appearance | DVS Hygroscopicity (%) | DSC ($T_{peak}$ °C.) | Mass loss (%) | HPLC purity (area %) |
|---|---|---|---|---|---|
| CPME | Off-White powder | 10 | 122 209 | 7 13 | 80 |

Figure 4:
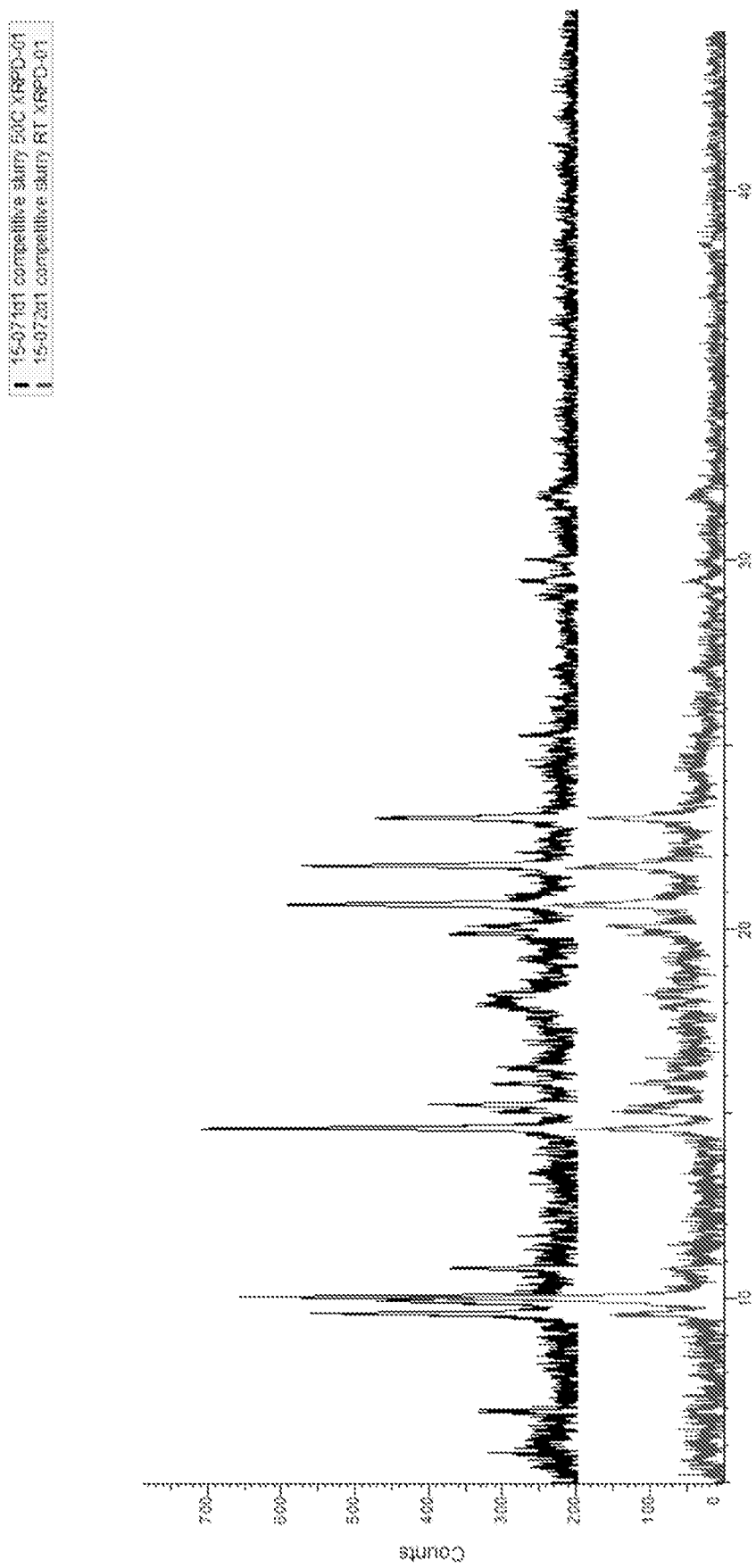
FIG. 4 depicts an X-ray powder diffraction patterns obtained from ITI-007 hydrochloride salt competitive slurry experiments in 1-butanol (top: 50° C.; bottom: RT).

Example 5: Competitive Stability Test of Hydrochloride Crystal Salt Polymorphs To determine the most stable of the three hydrochloride crystal salt polymorphs, a competitive slurry in 1-butanol is performed. Equal masses of the three polymorphs obtained according to Examples 2-4 above are mixed and slurried at room temperature and at 50° C. for 24 hours. XRPD analysis is then performed. Both slurry conditions result in a new crystalline pattern, suggesting the formation of a new solvate form. The XRPD spectra are shown in FIG. 4 (top: 50° C.; bottom: RT). DSC/TGA analysis shows two endothermic events, the first at $T_{onset}$=142° C., $T_{peak}$=150° C. and ΔE=−14 J/g, and the second event at $T_{onset}$=203° C., $T_{peak}$=216° C. and ΔE=−17 J/g. The TGA profiles shows three mass losses. The first two of 6% and 8% correspond, respectively, to the two endothermic events. TGR-IR analysis shows the first two of these mass losses to be primarily 1-butanol and water, indicating that a 1-butanol solvate has formed. The third mass loss occurs above 240° C. and likely corresponds to decomposition.

The invention claimed is:

1. A hydrochloride salt of 1-(4-fluoro-phenyl)-4-((6bR, 10aS)-3-methyl-2,3,6b,9, 10,10a-hexahydro-1H,7H-pyrido[3',4':4,5]pyrrolo[1,2,3-de]quinoxalin-8-yl)-butan-1-one, wherein the salt is in crystalline form and wherein the crystalline form is selected from the group consisting of: polymorph 1 corresponding to FIG. 1, polymorph 2 corresponding to FIG. 2, or polymorph 3 corresponding to FIG. 3.

2. The salt according to claim 1 which is a salt crystal, characterized as polymorph 1 and having an X-ray diffraction pattern substantially corresponding to FIG. 1.

3. The salt according to claim 1 which is a salt crystal, characterized as polymorph 2 and having an X-ray diffraction pattern substantially corresponding to FIG. 2.

4. The salt according to claim 1 which is a salt crystal, characterized as polymorph 3 and having an X-ray diffraction pattern substantially corresponding to FIG. 3.

5. A pharmaceutical composition comprising a salt according to claim 1, in combination or association with a pharmaceutically acceptable diluent or carrier.

* * * * *